US010159592B2

(12) United States Patent
Ingimundarson et al.

(10) Patent No.: US 10,159,592 B2
(45) Date of Patent: Dec. 25, 2018

(54) SPINAL ORTHOSIS, KIT AND METHOD FOR USING THE SAME

(71) Applicant: Ossur Iceland ehf, Reykjavik (IS)

(72) Inventors: Arni Thor Ingimundarson, Gardabaer (IS); Harry Duane Romo, Aliso Viejo, CA (US); Valgeir Petursson, Reyjhavik (IS); Zachariah J. Klutts, Irvine, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 430 days.

(21) Appl. No.: 15/053,247

(22) Filed: Feb. 25, 2016

(65) Prior Publication Data

US 2016/0250061 A1 Sep. 1, 2016

Related U.S. Application Data

(60) Provisional application No. 62/260,165, filed on Nov. 25, 2015, provisional application No. 62/126,111, filed on Feb. 27, 2015.

(51) Int. Cl.
*A61F 5/02* (2006.01)

(52) U.S. Cl.
CPC ........... *A61F 5/022* (2013.01); *A61F 5/02* (2013.01); *A61F 5/028* (2013.01)

(58) Field of Classification Search
CPC .... A61F 5/055; A61F 5/05816; A61F 5/3707; A61F 5/012; A61F 5/05891;

(Continued)

(56) References Cited

U.S. PATENT DOCUMENTS

| 7,916 A | 1/1851 | Knapp |
|---|---|---|
| 61,487 A | 1/1867 | Vollschwitz |

(Continued)

FOREIGN PATENT DOCUMENTS

| AU | 20 1027 10 20 A1 | 2/2012 |
|---|---|---|
| AU | 20 1027 10 20 A2 | 2/2012 |

(Continued)

OTHER PUBLICATIONS

Partial International Search Report from PCT Application No. PCT/US2017/052143, dated Dec. 22, 2017.

(Continued)

*Primary Examiner* — Ophelia A Hawthorne
(74) *Attorney, Agent, or Firm* — Workman Nydegger

(57) ABSTRACT

A spinal orthosis includes a rear panel, and first and second belt members securing to the rear panel. The first and second belt members each define a first end secured to a first side of the rear panel and a second end having a foldable portion adapted to fold over a first surface of the first and second belt members and secure to the first surface to reduce a length of the first and second belt members. First and second front closures are secured to the second ends of the first and second belt members, respectively, and arranged for removably securing to one another to form a continuously circumferential loop with the rear panel and the first and second belt members. A kit or method may be provided for sizing the belt members with a sizing device for forming a predetermined distance between the first and second belt members.

19 Claims, 12 Drawing Sheets

(58) Field of Classification Search
CPC ...... A61F 5/05883; A61F 5/024; A61F 5/028; A61F 13/12; A61F 2007/0009; A61F 5/00; A42B 3/0473; A47C 7/383
See application file for complete search history.

(56) References Cited

U.S. PATENT DOCUMENTS

| | | |
|---|---|---|
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 507,172 A | 10/1893 | Shelden |
| 571,749 A | 11/1896 | Colton |
| 596,849 A | 1/1898 | Combier |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 746,563 A | 12/1903 | McMahon |
| 772,926 A | 10/1904 | Colton |
| 787,894 A | 4/1905 | Colton |
| 888,490 A | 5/1908 | Haas |
| 894,066 A | 7/1908 | Scapra |
| 980,457 A | 1/1911 | Toles |
| 1,124,596 A | 1/1915 | Dalpe |
| 1,316,915 A | 9/1919 | Meyer et al. |
| 1,393,188 A | 10/1921 | Whiteman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 2/1951 | Kludt et al. |
| 2,554,337 A | 5/1951 | Lampert |
| 2,630,801 A | 3/1953 | Mest et al. |
| 2,696,011 A | 12/1954 | Galdik |
| 2,749,550 A | 6/1956 | Pease |
| 2,775,767 A | 1/1957 | Gould |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,128,514 A | 4/1964 | Parker et al. |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,434,469 A | 3/1969 | Swift |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,603,316 A | 9/1971 | Lehman |
| 3,762,421 A | 10/1973 | Sax, Sr. |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabholz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zufich |
| 4,173,973 A | 11/1979 | Hendricks |
| 4,175,553 A | 11/1979 | Rosenberg |
| 4,230,101 A | 10/1980 | Gold |
| 4,261,081 A | 4/1981 | Lott |
| 4,285,336 A | 8/1981 | Oebser et al. |
| 4,322,092 A | 3/1982 | Feucht et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,494,536 A | 1/1985 | Latenser |
| 4,502,471 A | 3/1985 | Owens |
| 4,508,110 A | 4/1985 | Modglin |
| 4,531,515 A | 7/1985 | Rolfes |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A | 3/1986 | Wellershaus |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,655,201 A | 4/1987 | Pirmantgen |
| 4,658,807 A | 4/1987 | Swain |
| 4,660,302 A | 4/1987 | Arieh et al. |
| 4,677,699 A | 7/1987 | Barabe |
| 4,677,969 A | 7/1987 | Calabrese |
| 4,680,878 A | 7/1987 | Pozzobon et al. |
| 4,691,696 A | 9/1987 | Farfan De Los Godos |
| 4,696,291 A | 9/1987 | Tyo |
| 4,697,583 A | 10/1987 | Mason et al. |
| 4,697,592 A | 10/1987 | Maddux et al. |
| 4,719,670 A | 1/1988 | Kurt |
| 4,719,709 A | 1/1988 | Vaccari |
| 4,761,834 A | 8/1988 | Kolb |
| 4,796,610 A | 1/1989 | Cromartie |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,843,688 A | 7/1989 | Ikeda |
| 4,862,878 A | 9/1989 | Davison et al. |
| 4,870,761 A | 10/1989 | Tracy |
| 4,905,678 A | 3/1990 | Cumins et al. |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |

(56) References Cited

U.S. PATENT DOCUMENTS

| | | |
|---|---|---|
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spann et al. |
| 5,117,567 A | 6/1992 | Berger |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | DeWall |
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | Lebron |
| 5,259,833 A | 11/1993 | Barnett |
| 5,295,947 A | 3/1994 | Muncy |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,387,245 A | 2/1995 | Fay et al. |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | DeRoche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak, Sr. et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak, Sr. et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,695,452 A | 12/1997 | Grim et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord, Jr. et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,737,854 A | 4/1998 | Sussmann |
| 5,746,218 A | 5/1998 | Edge |
| 5,752,640 A | 5/1998 | Proulx |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,848,979 A | 12/1998 | Bonutti et al. |
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,967,998 A | 10/1999 | Modglin |
| 5,993,403 A | 11/1999 | Martin |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,110,138 A | 8/2000 | Shirley |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,190,343 B1 | 2/2001 | Heinz et al. |
| D438,624 S | 3/2001 | Reina |
| 6,206,932 B1 | 3/2001 | Johnson |

(56) References Cited

U.S. PATENT DOCUMENTS

| | | |
|---|---|---|
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,282,729 B1 | 9/2001 | Dikawa et al. |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,401,786 B1 | 6/2002 | Tedeschi et al. |
| 6,413,232 B1 | 7/2002 | Townsend et al. |
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,494,853 B1 | 12/2002 | Rossi et al. |
| 6,502,577 B1 | 1/2003 | Bonutti |
| 6,503,213 B2 | 1/2003 | Bonutti |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,656,144 B1 | 12/2003 | Coligado |
| 6,676,617 B1 | 1/2004 | Miller |
| 6,676,620 B2 | 1/2004 | Schwenn et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,787 B2 | 3/2004 | Jungkind et al. |
| 6,726,643 B1 | 4/2004 | Martin |
| 6,769,155 B2 | 8/2004 | Hess et al. |
| 6,770,047 B2 | 8/2004 | Bonutti |
| 6,790,191 B1 | 9/2004 | Hendricks |
| 6,802,442 B1 | 10/2004 | Thompson |
| D499,806 S | 12/2004 | Machin et al. |
| 6,827,653 B2 | 12/2004 | Be |
| D501,078 S | 1/2005 | Cabana |
| 6,893,098 B2 | 5/2005 | Kohani |
| 6,893,411 B1 | 5/2005 | Modglin |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth et al. |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,174 B2 | 6/2010 | Chang et al. |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 7,993,296 B2 | 8/2011 | Nordt, III et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,372,023 B2 | 2/2013 | Garth et al. |

(56) References Cited

U.S. PATENT DOCUMENTS

| | | |
|---|---|---|
| 8,381,314 B2 | 2/2013 | Takamoto et al. |
| 8,556,840 B2 | 10/2013 | Burke et al. |
| 8,597,222 B2 | 12/2013 | Lucero et al. |
| 8,657,769 B2 | 2/2014 | Ingimundarson et al. |
| 8,728,019 B2 | 5/2014 | Kruijsen et al. |
| 8,795,215 B2 | 8/2014 | Rossi |
| 8,893,312 B2 | 11/2014 | Takamoto et al. |
| 8,956,315 B2 | 2/2015 | Garth et al. |
| 9,370,440 B2 | 6/2016 | Ingimundarson et al. |
| 9,468,554 B2 | 10/2016 | Petursson et al. |
| 9,554,935 B2 | 1/2017 | Ingimundarson et al. |
| 9,572,705 B2 | 2/2017 | Ingimundarson et al. |
| 9,795,500 B2 | 10/2017 | Ingimundarson et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2003/0000986 A1 | 1/2003 | Smith |
| 2003/0028952 A1 | 2/2003 | Fujii et al. |
| 2003/0125650 A1 | 7/2003 | Grosso |
| 2003/0125705 A1 | 7/2003 | Ruman et al. |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0074365 A1 | 4/2006 | Brown |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2006/0254598 A1 | 11/2006 | Saul |
| 2006/0260620 A1 | 11/2006 | Kazerooni et al. |
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2008/0045873 A1 | 2/2008 | Zours |
| 2008/0091132 A1 | 4/2008 | Bonutti |
| 2008/0195010 A1 | 8/2008 | Lai et al. |
| 2008/0208090 A1 | 8/2008 | Vollbrecht |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1 | 7/2009 | Garth |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |
| 2010/0204630 A1 | 8/2010 | Sandifer et al. |
| 2010/0205713 A1 | 8/2010 | Takamoto et al. |
| 2010/0217167 A1 | 8/2010 | Ingimundarson et al. |
| 2010/0228170 A1 | 9/2010 | Imai |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0292622 A1 | 11/2010 | Weissleder et al. |
| 2010/0299959 A1 | 12/2010 | Hammerslag et al. |
| 2010/0318010 A1 | 12/2010 | Sandifer et al. |
| 2011/0000005 A1 | 1/2011 | Brown |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0137221 A1 | 6/2011 | Brown |
| 2011/0144551 A1 | 6/2011 | Johnson |
| 2011/0152737 A1 | 6/2011 | Burke et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0022420 A1 | 1/2012 | Sandifer et al. |
| 2012/0029404 A1 | 2/2012 | Weaver, II et al. |
| 2012/0197167 A1 | 8/2012 | Kruijsen et al. |
| 2012/0204381 A1 | 8/2012 | Ingimundarson et al. |
| 2012/0220910 A1 | 8/2012 | Gaylord et al. |
| 2012/0232450 A1 | 9/2012 | Garth |
| 2012/0245502 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0174326 A1 | 7/2013 | Takamoto et al. |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0081189 A1 | 3/2014 | Ingimundarson et al. |
| 2014/0116452 A1 | 5/2014 | Ingimundarson et al. |
| 2014/0207040 A1 | 6/2014 | Ingimundarson et al. |
| 2014/0200121 A1 | 7/2014 | Von Hoffmann et al. |
| 2014/0207041 A1 | 7/2014 | Ingimundarson et al. |
| 2014/0336020 A1 | 11/2014 | Von Hoffmann et al. |
| 2014/0364786 A1* | 12/2014 | Haider .............. A61F 5/028 602/19 |
| 2016/0250061 A1 | 9/2016 | Ingimundarson et al. |

FOREIGN PATENT DOCUMENTS

| | | |
|---|---|---|
| AU | 20 1028 68 51 A1 | 3/2012 |
| AU | 20 1028 68 51 A2 | 5/2012 |
| CA | 2 112 789 A1 | 8/1994 |
| CA | 2 114 387 A1 | 8/1994 |
| CA | 2 767 353 A1 | 1/2011 |
| CA | 2 772 296 A1 | 3/2011 |
| CH | 577 282 A5 | 7/1976 |
| CH | 612 076 A5 | 7/1979 |

(56) References Cited

FOREIGN PATENT DOCUMENTS

| | | |
|---|---|---|
| CH | 624 001 A5 | 7/1981 |
| CN | 1311648 A | 9/2001 |
| CN | 1461190 A | 12/2003 |
| CN | 201101603 Y | 8/2008 |
| CN | 101444443 A | 6/2009 |
| CN | 101820783 A | 9/2010 |
| CN | 102470040 A | 5/2012 |
| DE | 1 197 192 B | 7/1965 |
| DE | 88 04 683 U1 | 6/1988 |
| DE | 38 22 113 A1 | 1/1990 |
| DE | 93 15 776 U1 | 2/1995 |
| DE | 295 03 552 U1 | 4/1995 |
| DE | 199 45 045 A1 | 3/2001 |
| DE | 202 04 747 U1 | 7/2002 |
| DE | 103 29 454 A1 | 1/2005 |
| DE | 20 2004 015 328 U1 | 2/2005 |
| DE | 20 2005 007 124 U1 | 6/2005 |
| DE | 20 2009 004 817 U1 | 9/2010 |
| DE | 202009004817 U1 | 9/2010 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 657 149 A1 | 6/1995 |
| EP | 0 589 232 B1 | 11/1995 |
| EP | 0 693 260 B1 | 9/1998 |
| EP | 0 651 954 B1 | 2/1999 |
| EP | 1 159 940 A2 | 12/2001 |
| EP | 1 236 412 A1 | 9/2002 |
| EP | 1 342 423 A1 | 9/2003 |
| EP | 1 588 678 A1 | 10/2005 |
| EP | 1 743 608 A2 | 1/2007 |
| EP | 1 985 264 A1 | 10/2008 |
| EP | 2 200 545 A1 | 6/2010 |
| EP | 2 451 412 A1 | 5/2012 |
| EP | 2 473 072 A1 | 7/2012 |
| FR | 1 104 562 A | 11/1955 |
| FR | 2 757 073 A1 | 6/1998 |
| FR | 2 952 807 A1 | 5/2011 |
| GB | 826 041 A | 12/1959 |
| GB | 909 970 A | 11/1962 |
| GB | 2 133 289 A | 7/1984 |
| JP | 3031760 U | 12/1996 |
| JP | H09-273582 A | 10/1997 |
| JP | H10-237708 A | 9/1998 |
| JP | 2000-290331 A | 10/2000 |
| JP | 2001-204851 A | 7/2001 |
| JP | 2003-175063 A | 6/2003 |
| JP | 2004-016732 A | 1/2004 |
| JP | 2004-041666 A | 2/2004 |
| JP | 2004-209050 A | 7/2004 |
| JP | 2007-291536 A | 11/2007 |
| JP | 3142546 U | 6/2008 |
| JP | 2009-082697 A | 4/2009 |
| JP | 2012-011550 A | 1/2012 |
| JP | 2013-503268 A | 1/2013 |
| JP | 2013-536010 A | 9/2013 |
| WO | 94/01496 A1 | 1/1994 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2005/086752 A3 | 4/2005 |
| WO | 2005/086752 A2 | 9/2005 |
| WO | 2006/121413 A1 | 11/2006 |
| WO | 2007003148 A1 | 1/2007 |
| WO | 2009/017499 A1 | 2/2009 |
| WO | 2009/017949 A1 | 2/2009 |
| WO | 2009/052031 A1 | 4/2009 |
| WO | 2009/068503 A1 | 6/2009 |
| WO | 2011/005430 A1 | 1/2011 |
| WO | 2011/025675 A1 | 3/2011 |
| WO | 2011/066323 A1 | 6/2011 |
| WO | 2012/029917 A1 | 3/2012 |
| WO | 2013/016670 A1 | 1/2013 |
| WO | 2016138215 A1 | 9/2016 |

OTHER PUBLICATIONS

International Search Report from PCT Application No. PCT/US2016/043505, dated Oct. 13, 2016.

Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993 concerning Medical Devices, 2 pages.

Mehlman, Charles T. et al., "Hyphenated History: Knight-Taylor Spinal Orthosis"; American Journal of Orthopedics; Jun. 2000; pp. 479-483, vol. 29, Issue 6.

Pamphlet—"Bledsoe Phillippon K.A.F. Positioning Kit", Bledsoe Brace Systems, Medical Technology Inc., 2004, 2 pages.

Posture Control Brace. Soft Form, Orthopaedic by Design, FLA Orthopedics, Inc., 1 page; 2004. http://www.flaorthopedics.com.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

Scoliosis Specialists. About the SpineCor Brace; 2006-2012; http://www.scoliosisspecialists.com/aboutspinecorbrace.html. Retrieved from Internet on Aug. 1, 2013.

Hsu et al., "Principles and Components of Spinal Orthoses", AAOS Atlas of Orthoses and Assistive Devices, 4th Ed., Chapter 7, 2008, pp. 89-111.

International Search Report and Written Opinion from Corresponding to International Application No. PCT/US2010/002893, dated Feb. 22, 2011.

International Search Report from PCT Application No. PCT/US2010/000601, dated Jun. 28, 2010.

International Preliminary Report on Patentability from PCT Application No. PCT/US2010/000601, dated Aug. 30, 2011.

International Search Report from PCT Application No. PCT/JP2011/069929, dated Oct. 18, 2011.

International Search Report and Written Opinion Issued in PCT/2012/024619, dated May 16, 2012.

International Search Report and Written Opinon of the International Searching Authority Issued in PCT/US2012/043252, dated Jan. 10, 2013.

International Search Report from Corresponding PCT Application No. PCT/US2013/021170 dated Apr. 12, 2013.

Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.

Sato, Ena et al., "Effect of the WISH-type hip brace on functional mobility in patients with osteoarthritis of the hip: evaluation using the timed Up & Go Test", Prosthetics and Orthotics International 2012 36:25 originally published online Nov. 17, 2011, http://poi.sagepub.com/content/36/125 [retrieved from internet on Jan. 22, 2014].

International Search Report from Corresponding PCT Application No. PCT/US2013/066425 dated Mar. 18, 2014.

Silosheath Brochure, Soft Socket Gel Liner, 4 pages, 1994.

International Search Report from International PCT Application No. PCT/US98/08975, dated Jul. 8, 1998.

Supplemental EP Search Report from EP Application No. 98920943, dated Dec. 7, 2004.

International Search Report from International PCT Application No. PCT/US2014/012860, dated Apr. 17, 2014.

Examination report from EP Application No. 12740242.8, dated Sep. 3, 2015.

Chinese Office Action from Chinese Application No. 201480017756.5, dated Jul. 29, 2016.

\* cited by examiner

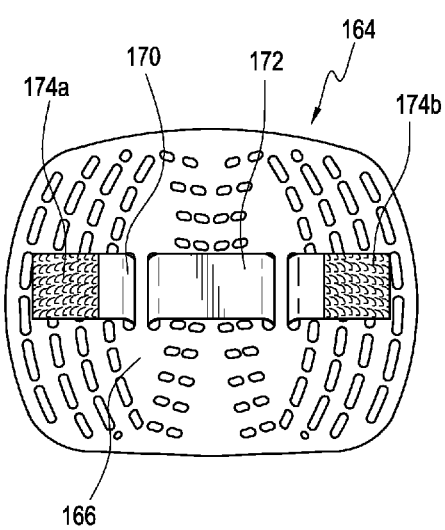
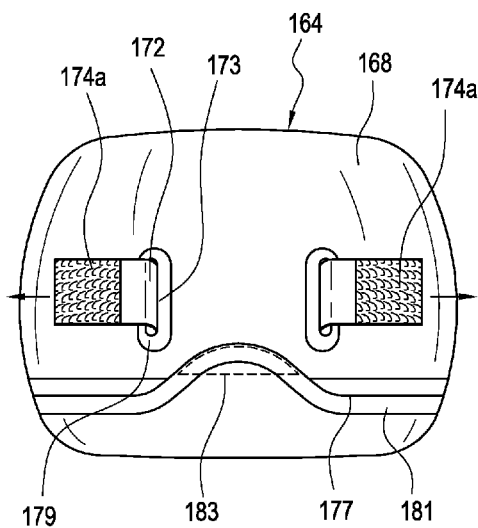
FIG. 10A                FIG. 10B
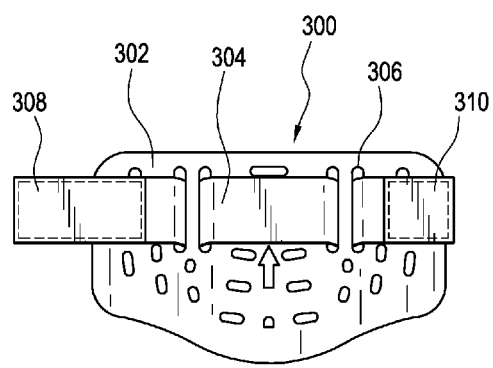
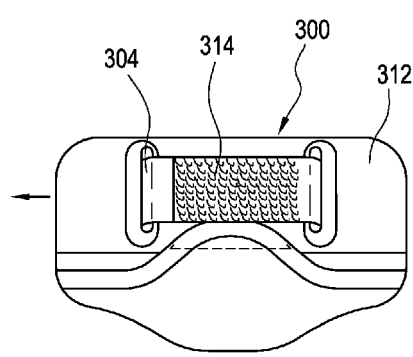
FIG. 10C                FIG. 10D

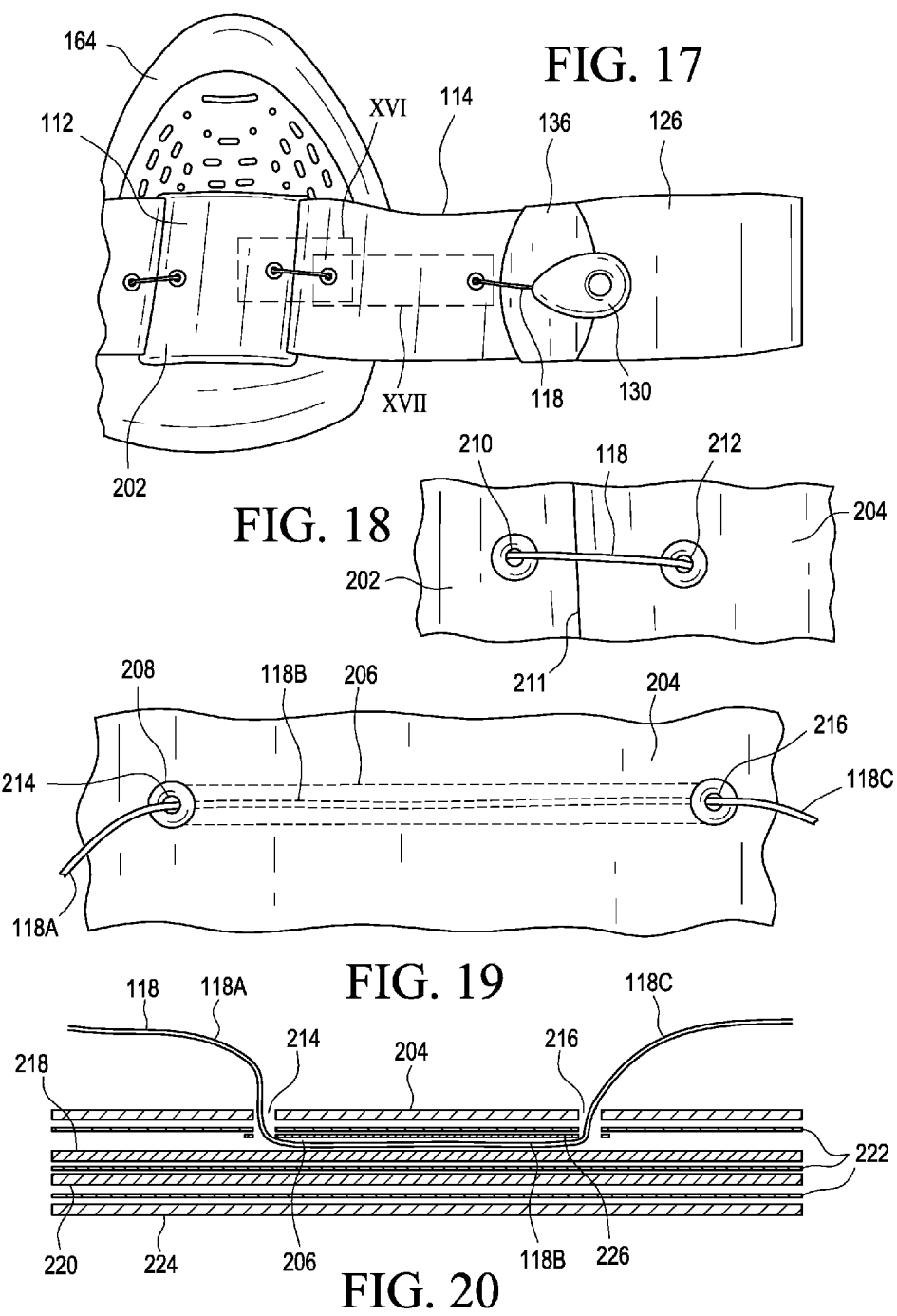

SPINAL ORTHOSIS, KIT AND METHOD FOR USING THE SAME

FIELD OF THE DISCLOSURE

The disclosure relates generally to orthopedic devices, and more specifically to a spinal orthosis.

BACKGROUND

A spinal orthosis or lumbar support is an orthopedic device designed for pain relief, protecting injured ligaments or muscles and post-surgical immobilization. A spinal orthosis is arranged to relieve pressure over the spinous processes while applying an even pressure to the paraspinal musculature to ensure comfortable and effective healing. Typical indications for spinal orthoses include spinal stenosis, herniated discs, post-surgical stabilization, stable and non-displaced spinal fractures, spondylolithesis, spondylolysis, and degenerative spinal pathologies.

In a known spinal orthosis in FIGS. 1-3, such as the exemplary spinal orthosis described in U.S. Pat. No. 8,172,779, granted on May 8, 2012 and incorporated by reference, the spinal orthosis has outer and inner side configurations 10A, 10B, with the inner side arranged to be adjacent the user's back. The orthosis has first and second belt members 12, 14, and a compression or closure system 16 adapted to exert pressure onto the lumbar region of a user's back. The compression or closure system 16 includes tightening elements or drawstrings 18 that permit the user to adjust pressure over the back and a cover 20 extending over the compression system 16.

A flexible or semi-rigid back plate 22 extends over at least part of the compression system 16, and is arranged to be adjacent the back of the user. The back plate 22 includes a posterior attachment system 24 for a rigid posterior panel 26, including a single hook and loop system connected at a single attachment point or flap 25 centered on the back plate 22. An anterior panel may be attached to the spinal orthosis at an anterior attachment system on one of the belts.

A requirement in a spinal orthosis is that they immobilize, at least in part, the torso, and stabilize the back. A factor in achieving this requirement is that the spinal orthosis is properly sized according to the anatomy of the user, and allows the user to effectively position and fasten the spinal orthosis.

It is desired to provide only a few spinal orthosis sizes. There is a need for a spinal orthosis that permits resizing of belt lengths to offer a "one-size-fits-all" spinal orthosis, including means, if necessary, to facilitate resizing of the spinal orthosis as a user undergoes size changes during rehabilitation.

SUMMARY

According to the embodiments described herein, a spinal orthosis is arranged for creating circumferential compression for a user, particularly in the lumbar region of the spine. The spinal orthosis enables saggital and/or coronal control, while offering a superiorly comfortable spinal orthosis. Indications for the spinal orthosis may include spinal stenosis, herniated disc, and degenerative spinal pathologies. The spinal orthosis may be combined with rigid panels for post-surgical stabilization; stable, non-displaced spinal fractures; spondylolisthesis; spondylolysis; spinal stenosis; herniated disc; and degenerative spinal pathologies.

Various embodiments are arranged with significant improvement over known spinal orthoses in donning and fitting processes. The donning and fitting processes may be made without measurements, and catered to anatomy and changing anatomy of a given user. The donning and fitting is arranged so it can be done on the actual user and thereby particularly customized for optimal fit and performance. No trimming is required for donning and fitting to a user, and no complicated fasteners or buckles are required for donning and fitting to a user. The length of the belt members can be increased, such as with belt extenders, or reduced, by folding, from an initial length, and such initial length can always be preserved for further adjustment of an actual length (such as including belt extenders or being folded and attached) of the belt member in the context of wearing the belt members.

The embodiments are arranged with flexible and breathable materials having improved performance over known spinal orthosis, including ventilation features offering optimal breathability in strategic locations. The spinal orthosis is arranged to accommodate many sizes by having means for expanding belt member lengths. The embodiments possess streamlined features which reduce weight, size and bulk over known spinal orthoses.

According to an embodiment of a spinal orthosis, the spinal orthosis includes a rear panel having first and second sides, and first and second belt members securing to the rear panel. The first belt member defines a first end secured to a first side of the rear panel and a second end having a foldable portion adapted to fold over a first surface of the first belt member and secure to the first surface to reduce a length of the first belt member. The second belt member has a first end secured to a second side of the rear panel and a second end having a foldable portion adapted to fold over a first surface of the second belt member and secure to the first surface to reduce a length of the second belt member. First and second front closures are securable to the second ends of the first and second belt members, respectively, and arranged for removably securing to one another to form a continuously circumferential loop with the rear panel and the first and second belt members.

The first front closure may include a locking element defined on a first side and arranged to engage a corresponding slot defined on a first side by the second front closure for securing the first and second belt members to one another. The first front closure defines a pocket along a first side, and configured and dimensioned for inserting at least a finger thereinto for locating a second end of the first front closure relative to the second end of the second belt member. The front closures may define first and second clamping sections arranged to removably secure to opposed sides of the foldable portions of the belt members.

The second ends of the first and second belt members may each include fasteners extending from an outer side of the spinal orthosis for securing to a surface of the first and second belt members on the outer side of the spinal orthosis. For example, an entirety or substantial entirety (such as areas with the exception of the fasteners or ventilation features) of the belt members may be formed from hook receivable material. At least one surface of the belt members, such either an outer surface or an inner surface opposite the outer surface and intended to be adjacent and face the body of the user, may define hook receivable material. The fasteners may be hook material that can engage along the length between the fasteners and the rear panel of the belt members themselves to allow for significant sizing of the belt members beyond predetermined settings of a small group of selections, as in the prior art.

The belt members are preferably of low profile in height and thickness. For example, the first and second belt members have a thickness in the range of 1 to 5 mm, and more preferably in the range of 1.5 to 2.5 mm. The belt members may be devoid of padding or spacer material, as in the prior art, and rather rely on both surfaces being formed by hook-receivable material with a substantially thin thickness, identified as being within the range noted above. The belt members may include ventilation features defined by the belt members themselves, such that the belt members are continuously constructed from the same material between the first and second ends. The ventilation features may include perforations of a defined shape and size, and may include a region thereabout having a reduced thickness from the remainder of the thickness of the belt members. The belt members may include reduced thickness regions without the perforations, to facilitate bending of the belt members and contribute to overall comfort and compliance of the belt members to the user.

The rear panel preferably includes a closure system having at least one tensioning element with a handle. The at least one tensioning element extends from the closure system and the handle is removably securable to a first surface of the first front closure. A rigid posterior plate having a connector may removably secure to an inner side of the rear panel to relieve pressure over spinous processes while applying an even pressure to paraspinal musculature to ensure comfortable and effective healing. Similarly, a rigid anterior plate may be secured to the inner side of the belt members at the anterior side of the spinal orthosis. These rigid plates may be added or removed depending on the motion restriction and compression desired during a rehabilitation period.

In an embodiment, the rear panel includes a stretchable cover extending from the first and second sides. The cover is arranged for stretching or retracting over a variable distance according to adjustment of the closure system. The first and second belt members may be formed from a substantially non-stretchable material such that pulling the second ends of the first and second belt members causes the variable distance to increase, and releasing the second ends causes the cover to retract to a predetermined distance.

The rear panel includes a closure system and a first end of an elongate tensioning element engages the closure system, and a handle secures to a second end of the tensioning element. The first belt member forms a channel including a first opening proximate the closure system and a second opening. The channel is formed between first and second surfaces of the first belt member such that the tensioning element enters the channel at the first opening and exits by the second opening such that the second end of the tensioning element extends beyond the second opening.

The spinal orthosis may be provided as a kit including a rear panel having first and second sides, a first belt member having a first end secured to a first side of the rear panel and a resizable second end, and a second belt member having a first end secured to a second side of the rear panel and a resizable second end. A sizing device has first and second positioning elements for establishing a clearance defined by a predetermined distance between the second ends of the first and second belt members. The predetermined distance allows for same front closures to be used generally regardless of the length of a user's waist, such that the front closures do not require any trimming.

In an embodiment, the first and second positioning elements are first and second rods spaced apart by a cord having a length extending the predetermined distance between the first and second rods. In another embodiment, the sizing device is a board having a main portion and the first and second positioning elements extend from the main portion. The first and second positioning elements are spaced apart by a center section with a width forming the predetermined distance. First and second grooves are formed by the board and separate the first and second positioning elements, respectively, from the center section. The kit may include first and second belt expanders arranged for securing to the second end of the first and second belt members. The first and second belt expanders have first and second ends each bearing fasteners for securing to the first and second belt members.

A method for resizing a spinal orthosis comprises the steps of using a sizing device having first and second positioning elements for establishing a predetermined distance between the second ends of the first and second belt members. The method includes extending a portion of the second end of the first belt member over the first positioning element to determine a resized length of the first belt member between the rear panel and the first positioning element. The second end of the first belt member is secured over a peripheral surface of the first belt member to retain the resized length of the first belt member and form a foldable portion of the first belt member. The sizing device is removed after the resized length is established. A first front closure is secured to the foldable portion of the first belt member. A portion of the second end of the second belt member is extended over the second positioning element to determine a resized length of the second belt member between the rear panel and the second positioning element.

These and other features, aspects, and advantages of the present disclosure will become better understood regarding the following description, appended claims, and accompanying drawings.

BRIEF DESCRIPTION OF THE DRAWINGS

FIG. 10A is a plan view of a posterior panel for use with the spinal orthosis embodiments.

FIG. 10B is a plan view of a posterior panel of FIG. 10A including a cover.

FIG. 10C is a plan view of an anterior panel for use with the spinal orthosis embodiments.

FIG. 10D is a plan view of the anterior panel of FIG. 10C including a cover.

FIG. 17 is a plan view of the spinal orthosis of FIG. 7A including channels for a tensioning element.

FIG. 18 is a detail view of a first channel in FIG. 17.

FIG. 19 is a detail view of a second channel in FIG. 17.

FIG. 20 is a cross-sectional schematic view of the belt member in FIG. 19 including the second channel.

Figure 1:
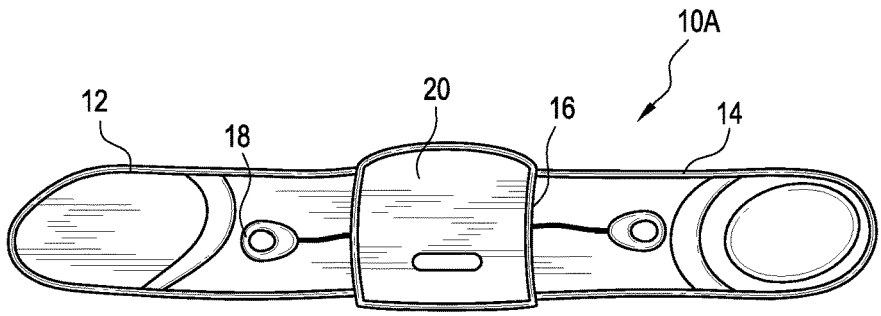
FIG. 1 shows an outer side of a prior art spinal orthosis.
Figure 2:
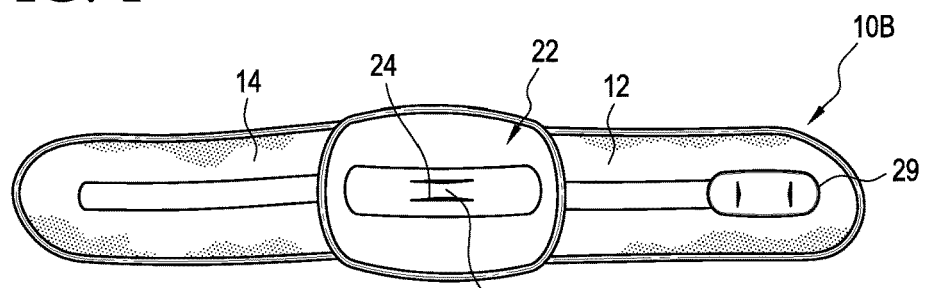
FIG. 2 shows an inner side of the prior art spinal orthosis of FIG. 1.
Figure 3:
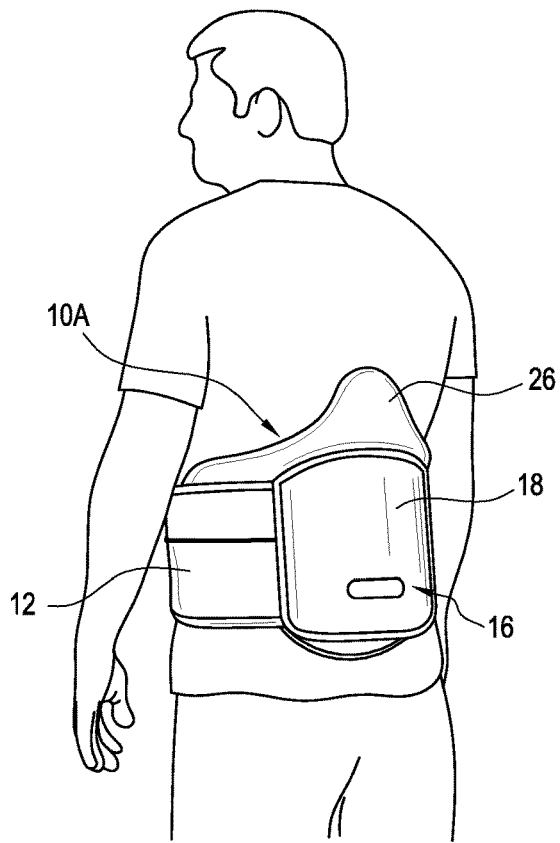
FIG. 3 is a perspective view of the prior art spinal orthosis of FIG. 1 having a posterior panel and placed on a user.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the specific embodiments disclosed, but on the contrary, the disclosure covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

Figure 4:
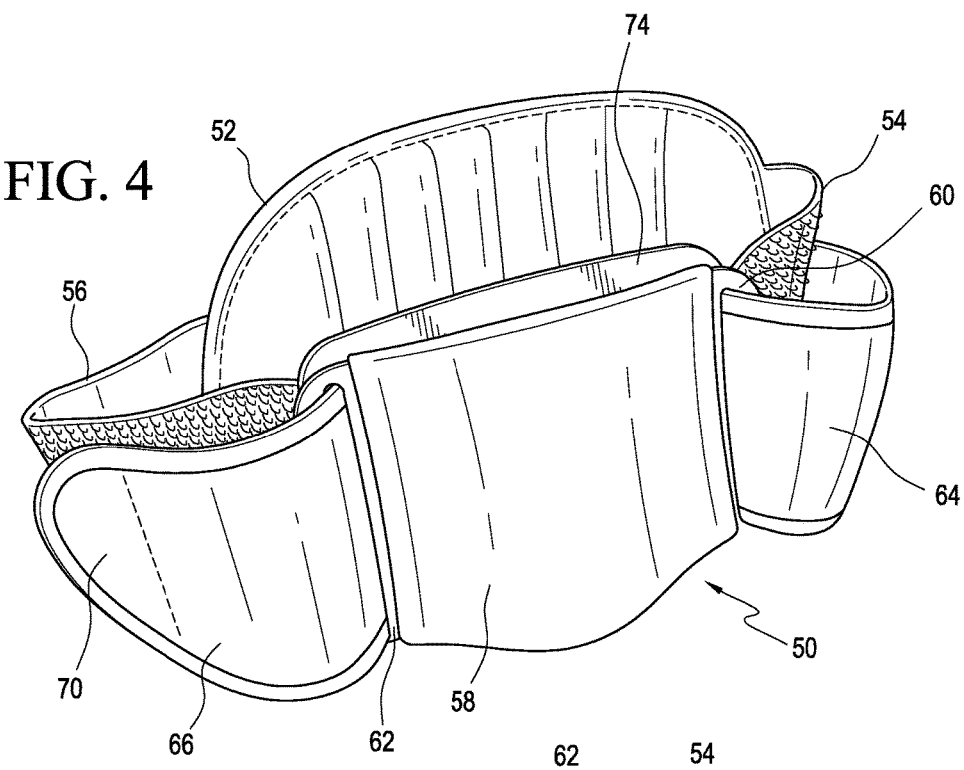
FIG. 4 is a perspective view of an embodiment of a spinal orthosis.
Figure 5:
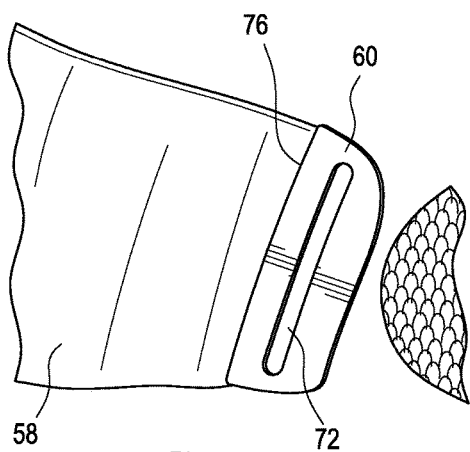
FIG. 5 is a detail view of a ring of a front panel in the embodiment of FIG. 4.
Figure 6:
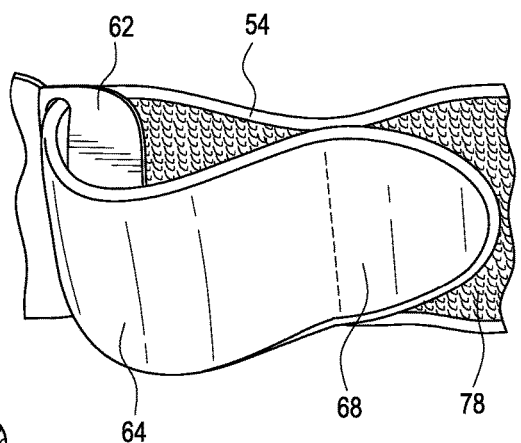
FIG. 6 is a detail view of a belt member extending through the ring of FIG. 5 and securing to itself.

FIGS. 4-6 illustrate an embodiment of a spinal orthosis 50 having a posterior panel 52 and first and second belt members 54, 56 extending therefrom. An anterior panel 58 includes first and second rings 60, 62 having apertures 72 through which the first and second belt members 54, 56 extend. The first and second belt member 54, 56 include first and second folded parts 64, 66 that extend over the first and second rings 60, 62, in which end portions 68, 70 secure to outer surfaces 78 of the first and second belt members 54, 56. The first and second rings 60, 62 flexibly extend from the anterior panel 58 along a flexible joint 76 to permit adjustment of the first and second belt members 54, 56 relative to the anatomy of the user. A rigid anterior plate 74 may be secured to the anterior panel 58.

The spinal orthosis 50 may include a compression or closure system (not shown) proximate the posterior panel as taught in U.S. Pat. No. 8,172,779 or U.S. patent application publication 2014/0207041, published on Jul. 24, 2014 and incorporated by reference. The spinal orthosis may be provided without the posterior panel, and only a compression system at the posterior side such that the spinal orthosis forms a continuous circumference with the compression system, the first and second belt members, and the anterior panel, as generally shown in FIG. 4.

The anterior panel 58 may be flexible, and can be either stretchable or non-stretchable. In the depicted embodiment, the anterior panel 58 is preferably non-stretchable so the first and second belt members 54, 56 may be tensioned over the first and second rings 60, 62, as they are folded over the first and second rings 60, 62 and secured to the outer surface 78 of the belt members.

As depicted in FIG. 6, the folded part 64 extends over and along the outer surface 78 of the first belt member 54. This enables quick adjustment for the user as the user only needs to insert the end portion 68 under the first ring 60 and secure the end portion 68 onto the outer surface 78 of the first belt member 68. The user can adjust the tension of the first belt member by removing the end portion and readjusting on the fly without having to take off the spinal orthosis.

According to the depicted embodiment, the outer surface of the belt members includes hook receivable or loop material, and the end portions of the belt members include hook material engageable with the material of the outer surface of the belt members. In this variation, the excess lengths of the belt members extending from the rings do not pile up to create pressure points along the circumference of the spinal orthosis directly adjacent the user.

The spinal orthosis is not limited to securing the end portions 68, 70 of the first and second belt members 54, 56, and may be secured along an inner surface of the belt members in a reverse manner to the aforementioned method. The inner surface of the belt members may include hook receivable material, and the end portions are rearranged accordingly with hook material. In this variation, the end portions are located on the inner side of the spinal orthosis and reduce the possibility of leaving excess length of the belt members on the exterior of the spinal orthosis.

Figure 7A:
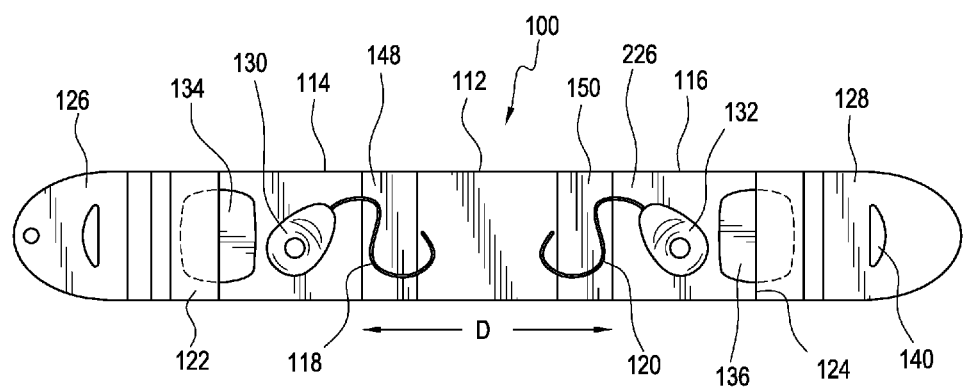
FIG. 7A is a plan view of another embodiment of a spinal orthosis.
Figure 8:
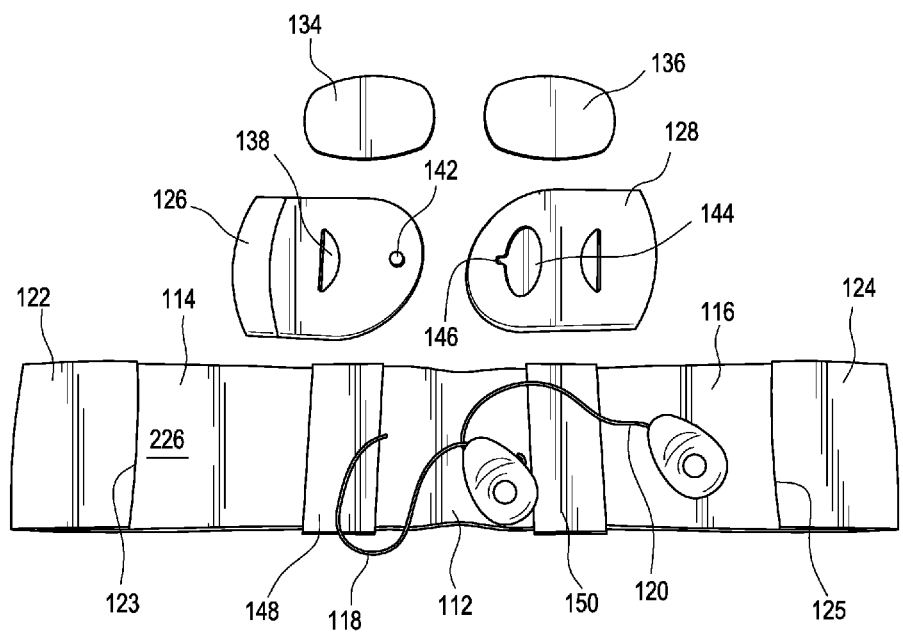
FIG. 8 is a perspective plan view of various detachable components in the spinal orthosis of FIG. 7A.

FIGS. 7A and 8 show a spinal orthosis 100 including a rear panel 112 having first and second sides. A first belt member 114 has a first end secured to a first side of the rear panel 112 and a second end 123 is configured to have a foldable portion 122 adapted to fold over a surface 226 of the first belt member 114 to reduce a length of the first belt member 114. A second belt member 116 has a first end secured to a second side of the rear panel 112 and a second end 125 configured to have a foldable portion 124 adapted to fold over a surface 226 of the second belt member 116.

While the surface 226 in FIGS. 7A and 8 is shown as the outer peripheral surface of the spinal orthosis, the spinal orthosis may be configured so the foldable portions 122, 124 go over an inner peripheral surface of the spinal orthosis. The outer peripheral surface is the surface defined as being opposite the inner peripheral surface arranged adjacent the anatomy of the user.

The first and second belt members 114, 116 may be removably secured to the rear panel 112 by first and second flaps 148, 150 extending from the first side of rear panel 112, or securable to the first and second belt members 114, 116 and the first and second sides of the rear panel 112. Alternatively, the first ends of the first and second belt members 114, 116 may be permanently secured to the first and second sides of the rear panel 112, such as by stitching or other appropriate means.

First and second patches 134, 136 may secure to the foldable portions 122, 124 of the first and second belt members 114, 116 and a surface 226 of the first and second belt members 114, 116 to maintain an adjusted length of the first and second belt members 114, 116 obtained by selectively arranging the length of the foldable portions 122, 124. Other methods and structures may be used rather than the patches, such as snaps or other locking elements selectively located along at least portions of the length of the belt members. The patches, however, omit the need for preselecting and limiting the amount of possible lengths as the length of the belt members is made substantially adjustable and is not limited to predetermined size settings.

First and second front closures 126, 128 secure over the foldable portions 122, 124 of the first and second belt members 114, 116. The first and second front closures 126, 128 are arranged to connect to the second ends 123, 125 of the corresponding belt members 114, 116. The front closures 126, 128 form a continuously circumferential loop with the rear panel 112 and the first and second belt members 114, 116 to completely encircle a user's torso and/or other proximate anatomy.

The first front closure 126 includes a locking element 142 defined on a second side and is arranged to engage a corresponding slot 144, 146 defined on a first side by the second front closure 128 for securing the first and second belt members 114, 116 to one another. The slot of the second front closure 128 defines an opening 144 and a keyhole 146 depending at a forward end of the slot proximate the first end of the second front closure 128. When the locking element 142 is inserted into the opening 144, it is directed and slips into the keyhole 146 which is sized and configured closely to the size of the locking element 142 to maintain engagement therewith. The opening 144 is sized greater than the keyhole 146, and on tensioning of the first and second belt members 114, 116 draws the locking element 142 toward the keyhole 146.

The locking element 142 and the slot enables quick and easy locking of the first and second front closures 126, 128, as well as quick and easy removal of the first and second front closures 126, 128 from one another. The locking element 142 and slot likewise require consistent donning and placement of the first and second front closures to one another, and require less strength and force for removal as compared to conventional methods such as using hook and loop systems. While the locking element and slot are preferred, they may be replaced with a hook and loop system with the first front closure including a hook section and the second front closure including a corresponding loop section for engagement with the hook section.

The first and second front closures 126, 128 define first and second pockets 138, 140 along a first side, and are configured and dimensioned for inserting at least a finger thereinto for locating a second end of the first front closure 126 relative to the second end of the second front closure 128.

Figure 11:
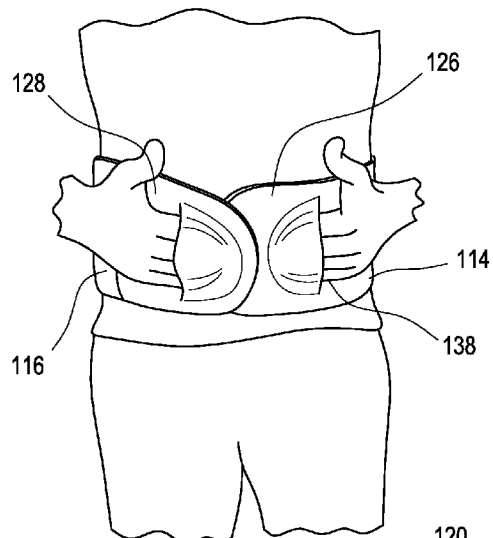
FIG. 11 is a schematic view of securing front closures to one another in the spinal orthosis of FIG. 7A.

As shown in FIG. 11, the pockets 138, 140 may be arranged to receive a hand of a user so as to remove the necessity of pulling the front closures toward one another, and are beneficial for geriatric users that may have difficulty pulling ends of the front closures with their fingers. The pockets ensure consistent placement of the user's hands for locking the locking element with the slot.

The rear panel 112 includes a compression system (not shown) and a stretchable cover 202 extending from the first and second sides. The cover 202 stretches or retracts over a variable distance D according to adjustment of the compression system. The compression system may be arranged in the same manner as discussed in connection with the spinal orthosis embodiment 50. The first and second belt members 114, 116 are formed from a substantially non-stretchable material such that pulling the second ends of the first and second belt members 114, 116 causes the variable distance D to increase, and releasing the second ends 123, 125 causes the cover 202 to retract to a predetermined distance D.

Figure 12A:
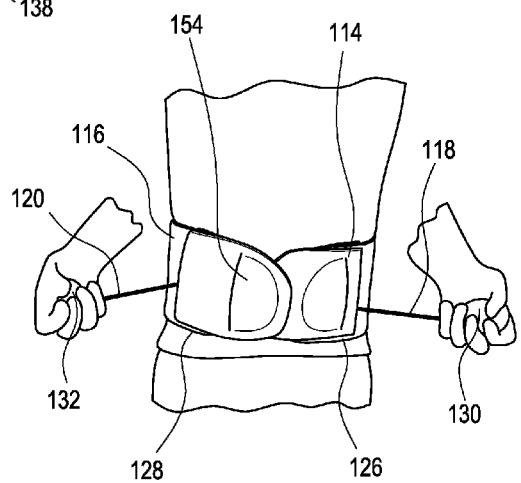
FIG. 12A is a schematic view of tightening tensioning elements in the spinal orthosis of FIG. 7A.
Figure 12B:
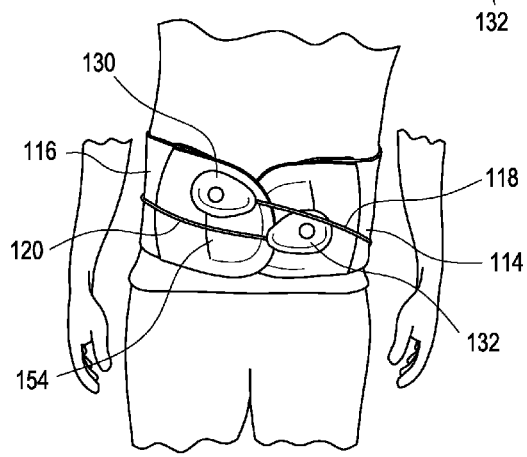
FIG. 12B is a schematic view of securing the tensioning elements to the front closures in the spinal orthosis of FIG. 7A.

First ends of elongate first and second tensioning elements 118, 120 engage the compression system, and first and second handles 130, 132 secure to second ends of the tensioning elements 118, 120. As shown in FIGS. 12A and 12B, the handles 130, 132 may secure to a surface of the first and second belt members 114, 116 and the first and second front closures 126, 128 for selective tensioning of the spinal orthosis by the compression system, as discussed in U.S. Pat. No. 8,172,779 or U.S. patent application publication 2014/0207041.

Figure 7B:
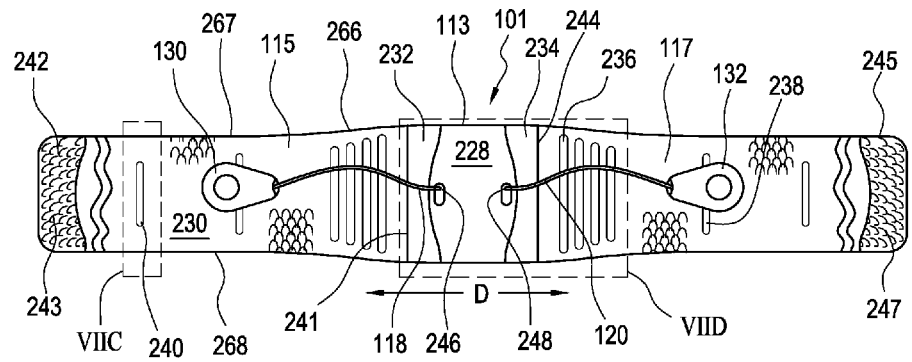
FIG. 7B is a plan view of another embodiment of a spinal orthosis.

FIG. 7B exemplifies another spinal orthosis embodiment 101 bearing similarity in part to the spinal orthosis 100 of FIG. 7A. In the embodiment of FIG. 7B, the spinal orthosis 101 includes a rear panel 113 having first and second sides. A first belt member 115 has a first end 241 secured to the rear panel 113 and a second end 242 bearing a fastener 243 for securing over a surface 230 of the first belt member. While the surface 230 is preferably an outer surface as compared to an inner surface directly facing and adjacent the user. The fastener 243 and the surface 230 preferably form a hook-and-loop fastener attachment system. A second belt member 117 similarly has a first end 244 secured to a second side of the rear panel 113 and a second end 245 with a fastener 247. The second belt member 117 has a same surface 230 as the first belt member 115, and likewise preferably forms a hook-and-loop fastener attachment system with the fastener 247. The spinal orthosis is envisioned as being modified so the fasteners 243, 247 can secure to the inner surface of the belt members, with the inner surface having hook receivable material.

As shown in FIG. 7B, both the fasteners 243, 247 of the second ends 242, 245 are located on the same side of the first and second belt members 115, 117. Both the first and second belt members 115, 117 are arranged to be reduced in length and the fasteners 243, 247 secured to the same side of the spinal orthosis on the surface 230. Such an arrangement is different from known spinal orthoses whereby the second side of a first belt member bears hook material, and the second side of a second belt member bears loop material for receiving hook material of the first belt member.

The first and second belt arms 115, 117 preferably have a first contour 266 tapering from first ends 241, 244 from the rear panel 113 and becoming linear in a second contour 267 toward the second ends 242, 245. The first contour 266 enables greater coverage over the posterior body part (i.e., back) of the user which undergoes compression by the spinal orthosis. As discussed in connection with FIG. 7D, the spinal orthosis includes a compression system that preferably includes a pulley set. The first contour 266 accommodates the pulley set, whereas the second contour provides a more streamlined and narrow belt configuration where less belt material is required.

Figures 7C, 7D:
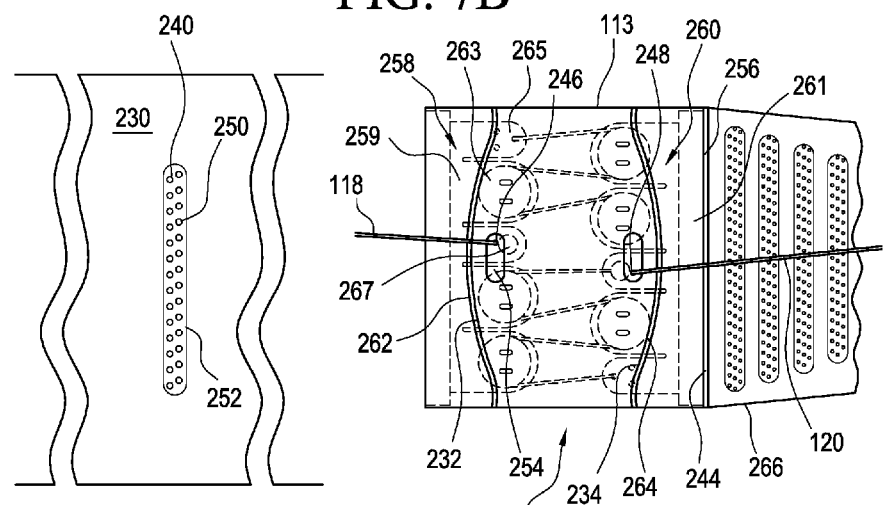
FIG. 7C is a detail view taken from VIIC in FIG. 7B.
FIG. 7D is a detail view taken from VIID in FIG. 7C.

Referring to FIGS. 7B and 7D, the spinal orthosis 101 includes first and second compression system covers 232, 234 secured to the first ends 241, 244 of the first and second belt members 115, 117, and either extend over the rear panel 113, or connect the first and second belt members 115, 117 thereto. The compression system covers 232, 234 have contours 262, 264 that taper to a center point along the height of the rear panel and flare toward upper and lower peripheral edges of the rear panel. The arrangement of the compression system covers 232, 234 is provided in part to maximize stretching of the rear panel 113 at the center point.

The rear panel 113 variably extends the distance between the compression system covers 232, 234, as noted above in connection with the embodiment of FIG. 7A. The rear panel 113 can be made from an elastic material, such as Spandex. The rear panel 113 defines openings 246, 248 through which the tensioning members 118, 120 extend from the compression system for selective securement onto the surface 230 of the belt members 115, 117, by the first and second handles 130, 132. The openings 246, 248, are preferably reinforced by a tape 254 laminated or welded to the material forming the rear panel 113.

The belt members and the compression system covers are preferably constructed from a sheet or laminated sheets of loop material. Unlike in many prior art spinal orthoses, the belt members of the spinal orthosis in FIG. 7B are substantially supple to enable folding of the belt members for resizing thereof. For example, the construction of the belt members may comprise at least two sheets of loop material formed by knitted fabric laminated to one another without other types of intermediate materials, such as spacer fabric in the prior art. This construction results in a substantially thin belt member while having some compressibility due in part to the loop material, and with both inner and outer surfaces of the belt members as having hook-receivable material by the loop material structure. Because both the inner and outer surfaces of the belt members is preferably constructed from hook-receivable material, there is a significant amount of space, such as along the foldable portions and outside the foldable portions, for securing the front closures to the belt members. Unlike the rear panel, the belt members are preferably not elastic, and stretchable.

Referring to FIGS. 7B and 7C, the first and second belt members 115, 117 preferably include perforated areas. For example, a first set of perforations 236 are defined proximate to the first ends 241, 244 of the first and second belt members 115, 117. The first set of perforations 236 cascade from the first ends 241, 244 and diminish in height substantially according to the taper of the first contour 266 of the belt members. Additional sets or individual perforations may be formed along the length of the belt members, such as a second set of perforations 238 generally located at a mid-length of the belt members, and a third set of perforations 240 generally located near the second ends 242, 245 of the belt members.

Each of the sets of perforations may define a plurality of perforations 250 preferably formed through the thickness of the belt members, and are distinguishable from porosity, weave, and structure of the belt members in that the perforations have a predetermined shape. The belt members may be embossed or have a reduced thickness area 252 about the sets of perforations. The reduced thickness area 252 is preferably oriented parallel to a height of the belt members, and may extend from one side or both sides relative to the thickness of the belt members. The reduced thickness area 252 is not limited to being arranged parallel to the height, but may be arranged in other desirable directions inclusive of being parallel to the length of the belt members. As depicted, the reduced thickness areas 252 preferably have a length shorter than the respective height of the belt members whereat the reduced thickness areas are located in order to maintain structural integrity of the belt members, although the reduced thickness areas may extend the entirety of the height of the belt members.

The sets of perforations 250 and the reduced thickness areas 252, either alone or in combination, may facilitate bending of the belt members and offer areas of enhanced breathability without substantially hindering the structural integrity of the belt members. As the belt members are substantially thin, they may have a thickness of 1 to 5 mm, and more preferably a thickness of 1.5 to 3.0 mm. The thickness at the reduced thickness areas may have a thickness of 0.5 to 1.5 mm.

FIG. 7D exemplifies the compression system 257 as having first and second pulley sets 258, 260. Each of the pulley sets 258, 260 define first and second panels 259, 261 which include an array of pulleys 263 about which both the first and second tensioning members 118, 120 rotate about. A first end of the tensioning members is anchored at an anchor 265 to one of the first and second panels, and extend through a respective guide 267 likewise formed on the first and second panels.

The first and second panels 259, 261 are considered "single" in that they include pulleys 263 for both the first and second tensioning members 118, 120, whereby some pulleys are individually dedicated for the first and second tensioning members. For example, the first tensioning member 118 is anchored to anchor 267 on the first panel 259, and extends through a first pulley on the second panel, is routed to a first pulley on the first panel, and back to a second pulley on the second panel, and finally then routed to the guide 267 on the first panel before extends from the exit hole 246 defined by the rear panel 113. The second tensioning member 120 is similarly routed between the first and second pulley sets as the first tensioning member 118, but is arranged about different pulleys located below the entirety of the pulleys about which the first tensioning member extends.

From the foregoing, it follows that adjustment of either of the first and second tensioning members 118, 120 will adjust the first and second panels 259, 261 to some degree since all of the pulleys are carried by the first and second panels. The length of the rear panel 113 and therefore the distance between the first and second panels 259, 261 will adjust according adjustment of at least one of the first and second tensioning members 118, 120.

The pulley panels 259, 261 are respectively secured to the first ends 241, 244 of the first and second belt members 115, 117 at an edge reinforcement or interface 256, along with ends of the rear panel 113 and the compression system covers 232, 234, which serve in part to reinforce the substantially thin and elastic material of the rear panel 113. The edge interface 256 may comprise stitching of the aforementioned components together as a unitary interface, or some components may be laminated or welded together or with others stitched to one another.

Figure 7E:
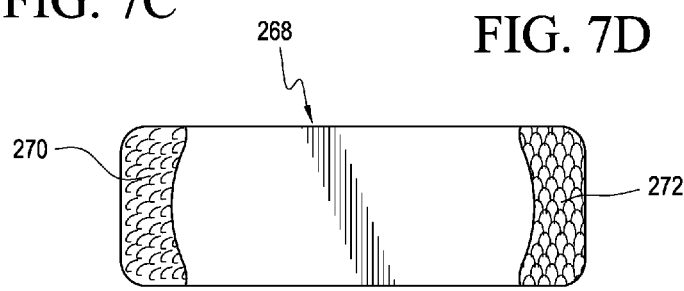
FIG. 7E is a belt expander for securing to the spinal orthosis of FIG. 7A.

FIG. 7E depicts a belt extender 268 that is arranged for extending a length of one of the belt members. The belt extender 268 includes a first end having a fastener 270, such as hook material, and a second end having a fastener 272, such as loop material. The second end 272 is shaped to correspond to the second ends 242, 245 of the belt members, and the fasteners 243, 247 disposed thereon for engagement therewith. The first fastener 270 takes the place of the fasteners 243, 247 at the first ends of the belt members when the second fastener 272 engages the belt members. The belt members between the first and second fasteners 270, 272 may be formed similarly as the same construction as the belt members. The first fastener 270 is preferably located on a different side of the second fastener 272, although the belt extender may be adapted so the first and second fasteners 270, 272 are on the same side.

Figure 9A:
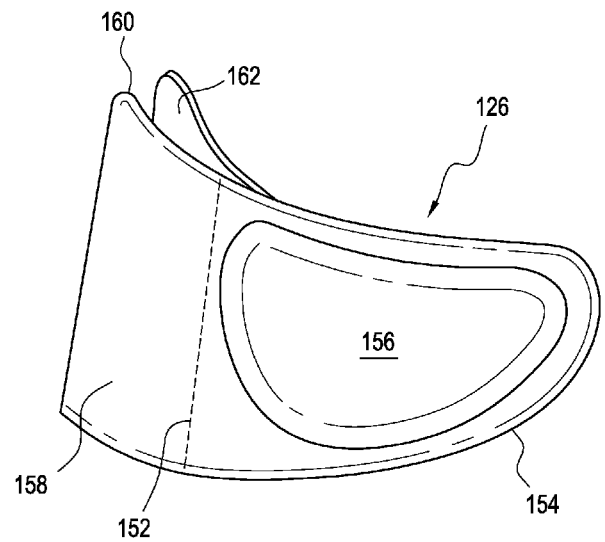
FIG. 9A is a perspective view of a front closure for use in the spinal orthosis of FIG. 7A.

Referring to FIG. 9A, an embodiment of the first front closure 126 defines first and second clamping sections 160, 162 at a rear section 158 arranged to removably secure to opposed sides of the foldable portion 122 of the first belt member 114 in FIG. 8. The first front closure 126 includes material 156 at least at the forward end 154 for receiving the handles in FIG. 8. The material 156 may spread across both the forward and rear sections 154, 158. The clamping sections 160, 162 may be modified over the description in U.S. patent application publication 2014/0081189, published Mar. 20, 2014, incorporated herein in its entirety, to accommodate foldable portions of a belt member rather than severed ends of a belt member.

Figures 9B, 9C:
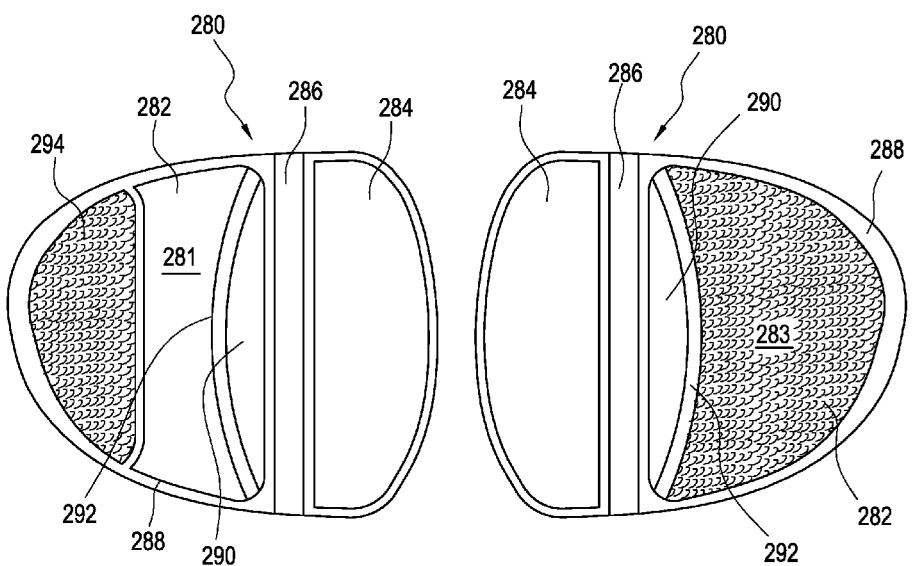
FIGS. 9B and 9C are plan views showing inner and outer sides of a front closure for the spinal orthosis embodiments.

FIGS. 9B and 9C depict another embodiment of a front closure 280 defining a first or leading section 282 for securing to a corresponding front closure on another side of the belt members or a belt member, a trailing section 284 for securing to the belt members, and a third section or divider 286 located between the first and second sections 282, 284. A peripheral portion 288 preferably extends about the first and second sections 282, 284, and is divided by the third section 286. The peripheral binding 288 may define a tapered and/or soft edge.

Both first and second sides 281, 283 of the front closure 280 define pockets 290 delimited by a pocket periphery 292. The first side 281 includes a fastener 294, preferably in the form of hook material but may include other know types of fasteners. The second side 283 likewise includes a fastener, preferably in the form of hook material formed by the surface of the front closure 280. The fastener 294 may engage the surface of the second side 283 or the material surface of the belt members.

Figure 9D:
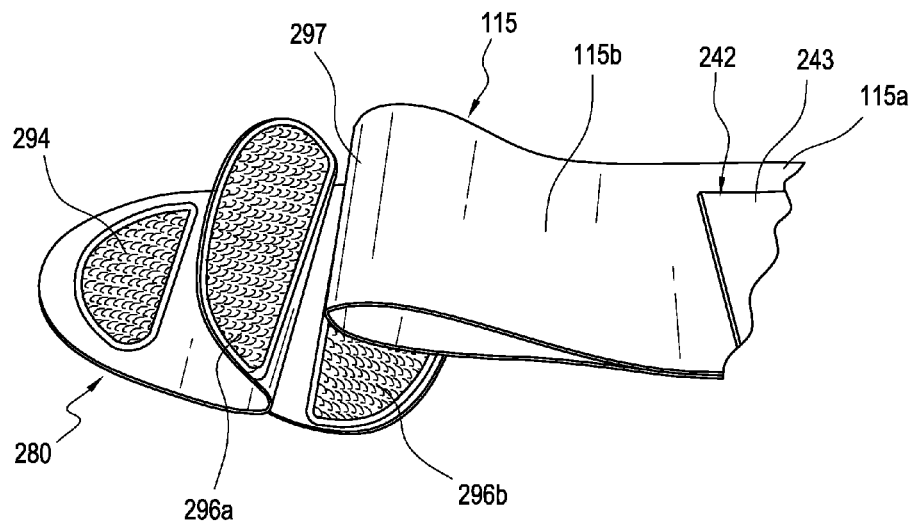
FIG. 9D is a schematic view showing attachment of the front closure in FIGS. 9B and 9C to a spinal orthosis.
Figure 9E:
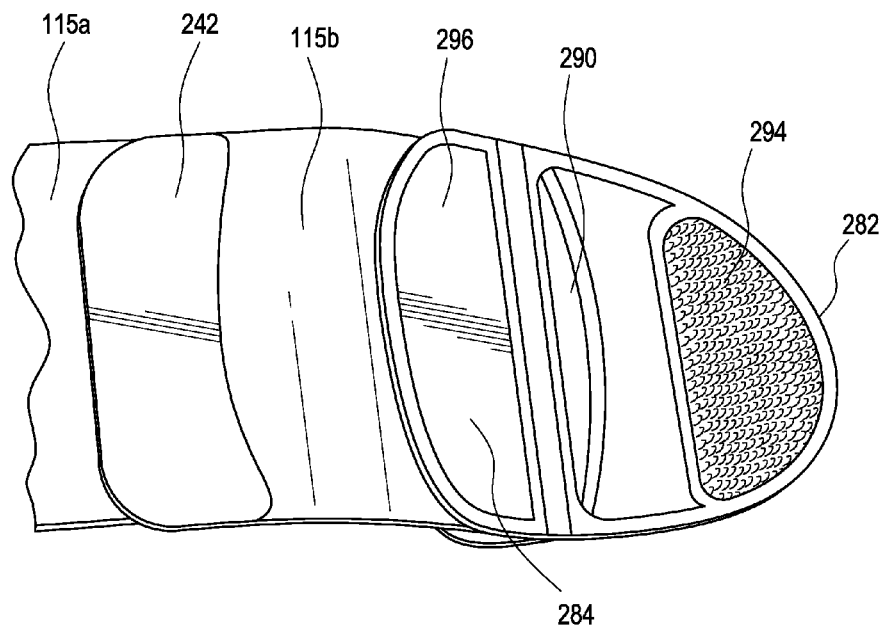
FIG. 9E is a schematic detail view showing the front closure in FIGS. 9B and 9C attached to the spinal orthosis.

FIGS. 9D and 9E exemplify how the front closure 280 secures to the belt members. The front closure 280 defines a clamp 296 at the second section 284, and is preferably defined by first and second flaps 296a, 296b bearing hook material that secures onto opposed sides of the belt member. The flaps 296a, 296b preferably extend and open to the third section 286 whereat the flaps 296a, 296b hinge from.

The second end 242 of the belt member 115 folds over itself at a selected length at a crease 297 with a first belt member segment 115a extending between the rear panel (not shown) to the crease 297 and a second belt member segment 115b extending from the crease 297 to the second end 242. The fastener 243 at the second end 242 secures to the belt member segment 115a. The flaps 296a, 296b secure to the belt member 115 at and over the crease 297 by engaging hook surface of the first belt member 115.

FIGS. 10A and 10B depict a supplementary panel 164 having a connector 172, such as a strap, arranged for removably securing to the compression system covers in the spinal orthosis of FIG. 7B or the belt members 115, 117 by fasteners 174a, 174b. The connector 172 is preferably elastic so that it can stretch or contract according to displacement of the variable clearance between the pulley sets and rear panel. The connector 172 is slidably retained to the supplementary panel 164 by at least one slot 170 through which the connector 172 extends. The at least one slot 170 enables the connector to stretch outwardly or away from the shell (as shown with the arrows) and contract without detriment to the supplementary panel.

The supplementary panel 164 preferably includes a plate 166 that may be apertured and is arranged to generally conform in geometry to a lower back or lumbar region for a user. The plate 164 preferably defines the at least one slot 170. The plate 166 may be substantially rigid or semi-rigid, or alternatively flexible but upon compression against a body part of a user rendered rigid.

The supplementary panel 164 includes a cover 168 which substantially or fully encases the plate 166. In the embodiment of FIG. 10B, the cover includes at least one slot 173 generally corresponding in location to the at least one slot 170 defined by the plate 166. The cover 168 defines a slit 177 enabling insertion and extraction of the plate 166 from the cover 168. The slit 177 preferably is releasably closeable with a fastener 183 keeping opposed sides of the cover 168 at the slit 177 secured to one another. Edge reinforcement 179 is provided about the at least one slot 173 and additional edge reinforcement 181 may be provided about the slit 177. The edge reinforcement 179, 181 may be a reinforcing film laminated or welded to the material forming the cover 168.

FIGS. 10C and 10D depict an anterior panel 300 arranged for securing to belt members, particularly near or at the second ends thereof. The anterior panel 300 includes a substantially rigid shell 302 and a connector 304 extending through at least one slot 306 formed by the shell 302. The connector 304 is preferably inelastic and has opposed ends 308, 310 which secure to one another to form a loop. When secured to one another, the opposed ends 308, 310 bear on an outer surface thereof a hook material 314 for securing to the first and second belt members. The anterior panel 300 may include a cover 312 arranged similarly to the cover for the supplementary panel 164.

Figures 10E, 10F:
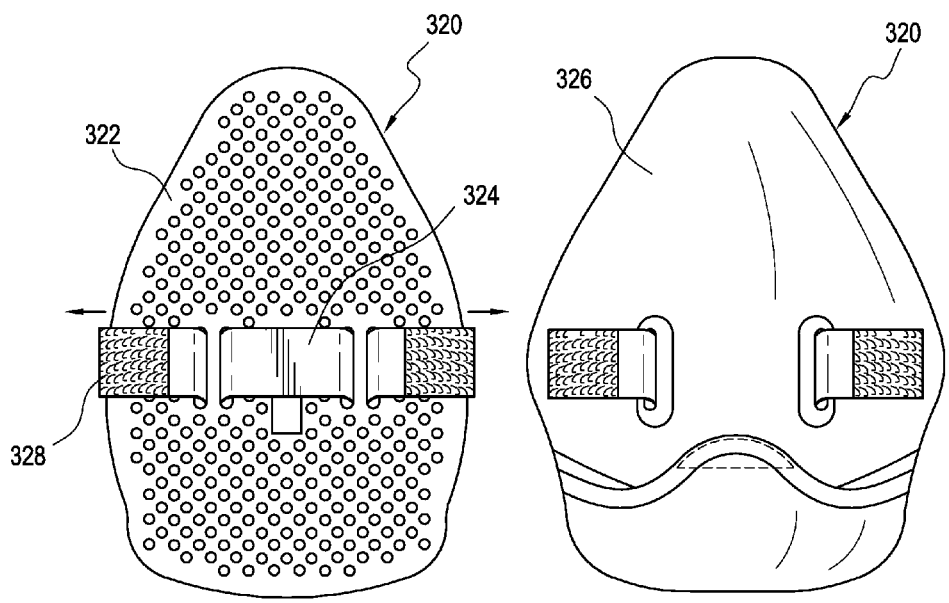
FIG. 10E is a plan view of another embodiment of a posterior panel for use with the spinal orthosis embodiments.
FIG. 10F is a plan view of the posterior panel of FIG. 10E including a cover.

FIGS. 10E and 10F illustrate a posterior panel 320 having a rigid shell 322 and a connector 324 bearing fasteners 328 similar to the supplementary panel 164 of FIGS. 10A and 10B for securing to the compression system covers. The posterior panel 320 likewise includes a cover 326 arranged similarly to the cover in the supplementary panel 164.

Figures 10G, 10H:
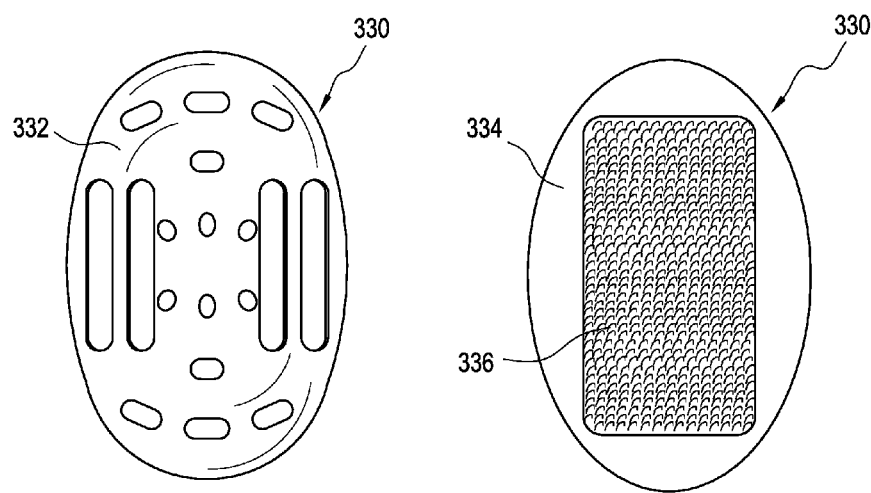
FIG. 10G is a plan view of a lateral panel for use with the spinal orthosis embodiments.
FIG. 10H is a plan view of the lateral panel of FIG. 10G including a cover.

FIGS. 10G and 10H depict a lateral panel 330 having a substantially rigid shell 332, and a removable cover 334 bearing a fastener 336. The lateral panel 330 is arranged for securing to the belt members between their first and second ends for providing lateral side support for the spinal orthosis.

The panels may be used as needed to achieve correct fit and positioning. The rigid posterior panel should be centered on the spine with the bottom of the posterior panel at approximately the sacroiliac joint. The rigid lateral panels should be placed on landing zones on the belt arms, which may be formed by the embossed or reduced thickness regions. The anterior panel should be centered on the abdomen with the bottom edge just above the symphysis pubis while still allowing the patient to sit comfortably.

The panels can be modified as necessary to optimize patient fit and comfort by removing them from their respective sleeves and adjust the panels with a heat gun and/or a trimming device. The spinal orthosis is a modular system and can be customized to the needs of the user. The panels can be added or removed depending on motion restriction and compression desired throughout a rehabilitation period. Any of the panels described herein may include any of the features of the plates or panels described in U.S. patent application publication 2014/0081189.

Figure 13:
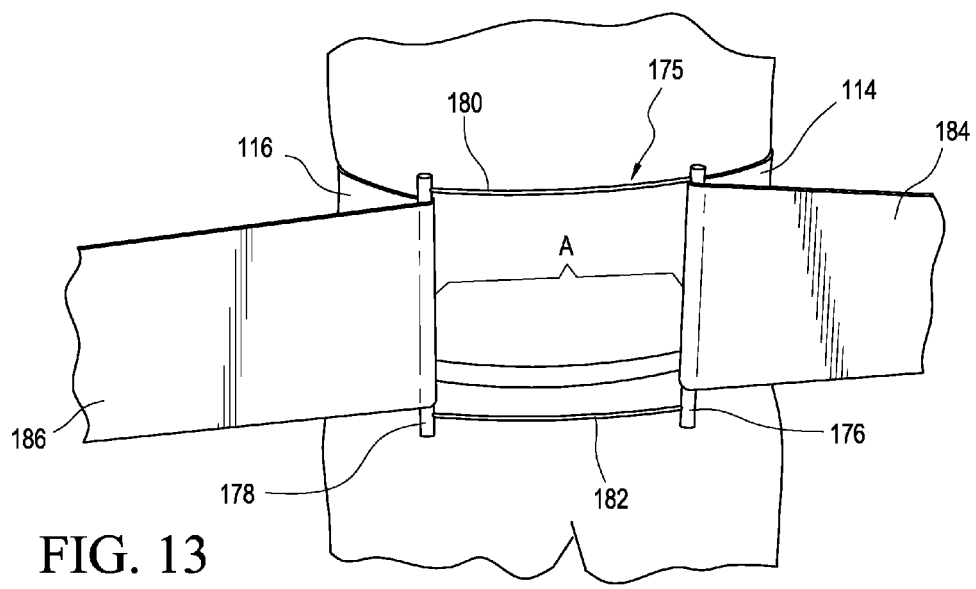
FIG. 13 is a schematic view showing a method and kit for resizing the spinal orthosis of FIG. 7A by pulling belt members away from a sizing device.
Figure 14:
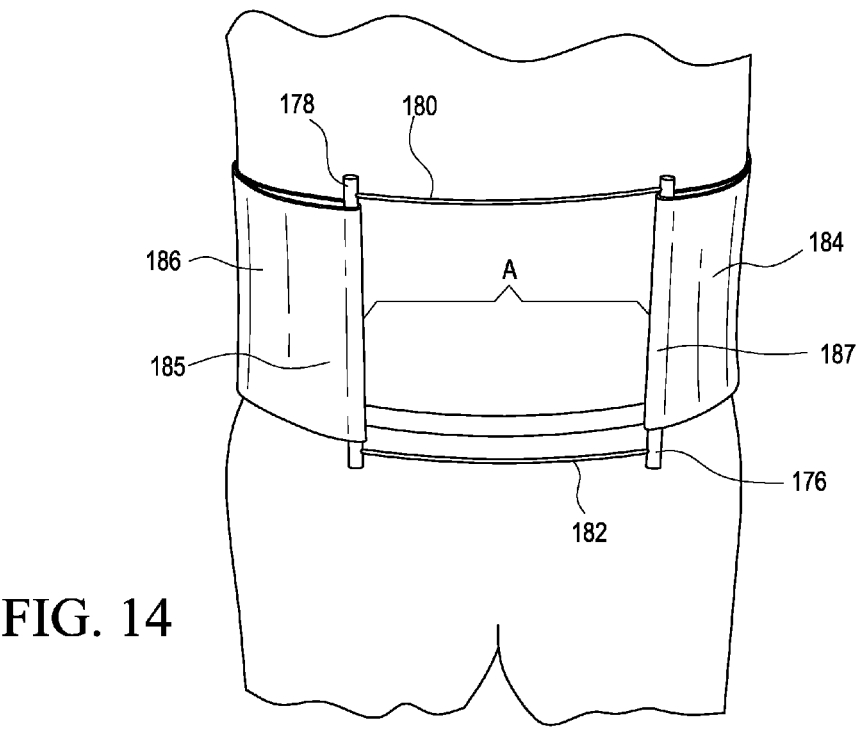
FIG. 14 is a schematic view showing the method of FIG. 13 wherein the belt members are tensioned.

FIGS. 13 and 14 depict a kit and method for sizing a lumbar belt having features of the spinal orthosis 100 of FIG. 7A by adjusting relative lengths of the first and second belt members. A sizing device 175 has first and second positioning elements 176, 178 for establishing a clearance defined by a predetermined distance (A) between the second ends of the first and second belt members 114, 116. The first and second positioning elements are first and second rods 176, 178 spaced apart by first and second cords 180, 182 each having a length (A) extending the predetermined distance between the first and second rods 176, 178.

As shown, the second ends of the first and second belt members 114, 116 are inserted and pulled over the first and second positioning elements 176, 178 to determine a resized length of the first and second belt members 114, 116 between the rear panel 112 and the first and second positioning elements 176, 178. The patches are used to secure the first and second foldable portions 184, 186, and pulled and tensioned about the first and second positioning elements 176, 178. The first and second belt members 114, 116 are resized to have a new length between the rear panel and an end of the foldable portions 185, 187.

Of note, the first and second foldable portions 184, 186 bear fastener material, as in the fasteners 243, 247 in the embodiment of FIG. 7B, so folded portions 185, 187 can extend outwardly (or inwardly) and be tensioned about the positioning elements 176, 178 in the same manner, such as extending from inside and over the positioning elements 176, 178, as in FIG. 13. By having both the foldable portions 184, 186 extending in the same orientation, the user can generally uniformly tension and size the length of the foldable portions 184, 186, as the first and second belt members 114, 116 will likewise have the same length after sizing of the foldable portions 184, 186.

The first and second front closures are secured on the resized first and second belt members, and the distance needed to accommodate the first and second front closures is assured by the length of the cords. An advantage to this kit and method is that the first and second belt members are sized without a need for trimming. The belt members can be resized according to different needs of a user, and any changes to the belt members can be redone, reversed and resized without the use of complicated buckles or fasteners.

Figure 15:
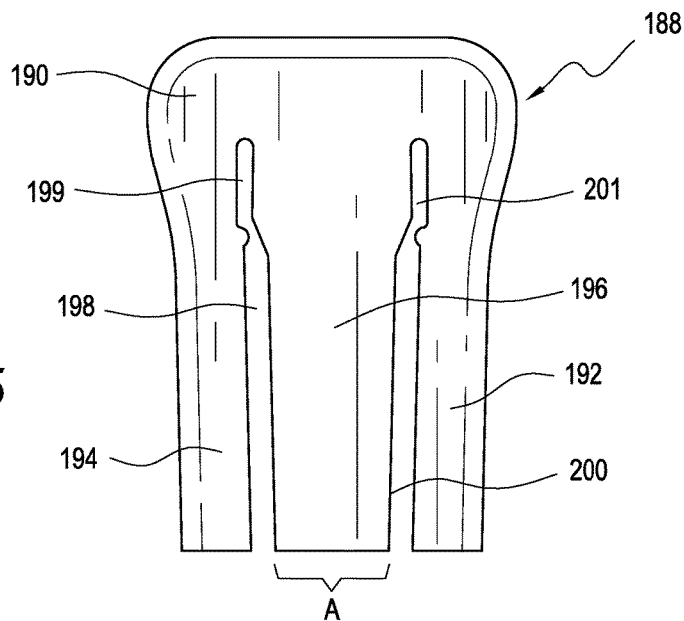
FIG. 15 is a plan view of an embodiment of a sizing device.
Figure 16:
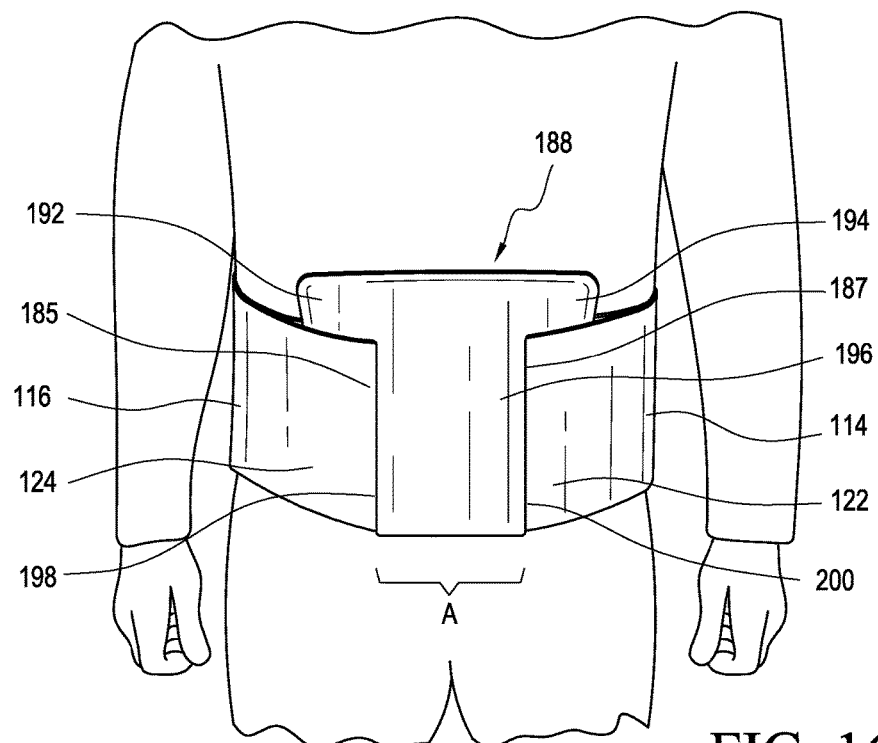
FIG. 16 is a schematic view of a user using the sizing device of FIG. 15.

Turning to FIGS. 15 and 16, another kit and method is provided for resizing the relative belt lengths of the first and second belt members for a user. In this kit, the sizing device 188 is a rigid board having a main portion 190 and the first and second positioning elements 192, 194 extend from the main portion 190. The first and second positioning elements 192, 194 are spaced apart by a center section 196 with a width or predetermined distance (A) forming the predetermined distance discussed above in connection with the sizing device 175. First and second grooves 198, 200 are formed by the board 188, and separate the first and second positioning elements 192, 194, respectively, from the center section 196. Each of the first and second grooves 198, 200 include upper grooves 199, 201 arranged to pinch the belt members to better retain them relative to the sizing device 188.

In the method shown in FIG. 16, sizing the lumbar belt using the sizing device 188 includes placing the first and second belt members 114, 116 through the grooves 198, 200, and drawing the foldable portions 122, 124 back toward the rear panel so they are tensioned against the first and second positioning elements 192, 194 and secured using various means described above. The folded portions 185, 187 are positioned apart the width (A) from one another for placement of the front closures.

FIGS. 17-20 illustrate how the belt members may have means for concealing various length segments of the tensioning element. For example, the first belt member 114 may form a channel 206 including first and second openings 214, 216 for concealing the tensioning element 118, in the form of a cable. The channel 206 is formed between first and second peripheral surfaces 204, 224 of the belt member 114.

FIG. 18 depicts a section of the rear panel having a panel material 202 surrounding the compression system, as discussed above. The panel material 202 may be preferably stretchable to accommodate activation of the closure system. The cable 118 extends from interior of the panel material 202 and exits from aperture 210. The cable 118 spans where the belt member and panel material 202 join at joint 211, and enters the belt member at an aperture 212. In this embodiment, the panel material and the belt are constructed differently, although the rear panel and belt member at the joint may be constructed to permit the cable to extend across the joint in a concealed manner.

Referring to FIG. 19, the cable 118 has a first portion 118A outside the channel 206 and proximate the first opening 214. A second portion 118B extends through the first aperture 214 and within the channel 206. A third portion 118C extends from the second aperture 216 and outside the channel 206. For any of the openings, an eyelet 208 may be provided to reinforce the material about the apertures.

Referring to FIG. 20, the belt member 114 may include a core including first and second core layers 218, 220 or a single substrate, and first and second layers 204, 224 forming the first and second peripheral surfaces such as outer and inner surfaces of the belt, respectively, and on opposed sides of the core 218, 220. A third layer 226 is secured to the first layer 204 whereby the channel 206 is located between the third layer 226 and the core layers 218, 220. The third layer 226 generally only extends between the first and second openings 214, 216 to reinforce the first layer and facilitate sliding of the cable.

The core 218, 220, and the first, second and third layers 204, 224, 226 are laminated to one another with exception of the third layer 226 to the core 218, 220 to permit opening of the channel 206. The first layer 204 is laminated to the core 218, 220 outside third layer 226. Adhesive layers 222 may be used to secure the various layers to one another through lamination.

The channel is advantageous in that it serves as a retainer of the cable, and reduces the amount of cable exposed to be tangled or snagged on external elements. The channel moves the exit point of the cable forward on the belt members which makes it easier for the user to find and see the cable. Various channels may be provided along the length of the belt members or a single, long channel may be formed.

The solution provided above eliminates a need for stitching, and instead relies on lamination of the layers. The channel is not limited to the solution provided above, and may indeed include channels formed by stitching of the layers of the belt members.

While the foregoing embodiments have been described and shown, alternatives and modifications of these embodiments, such as those suggested by others may be made to fall within the scope of the disclosure. While the spinal orthosis has been described in combination with a spinal orthosis, it will be understood that the principles described may be extended to other types of orthopedic and prosthetic devices.

The invention claimed is:

1. A spinal orthosis, comprising:
a rear panel having first and second sides;
a first belt member having a first end secured to the first side of the rear panel and a second end having a foldable portion adapted to fold over a first surface of the first belt member and secure to the first surface to reduce a length of the first belt member;
a second belt member having a first end secured to the second side of the rear panel and a second end having a foldable portion adapted to fold over a first surface of the second belt member and secure to the first surface to reduce a length of the second belt member;
first and second front closures are securable to the second ends of the first and second belt members, respectively, and arranged for removably securing to one another to form a continuously circumferential loop with the rear panel and the first and second belt members;
wherein the first front closure includes a locking element defined on a second side and arranged to engage a corresponding slot defined on a first side by the second front closure for securing the first and second belt members to one another.

2. The spinal orthosis of claim 1, wherein the first front closure defines a pocket along a first side and configured and dimensioned for inserting at least a finger thereinto for locating a second end of the first front closure relative to the second end of the second front closure.

3. The spinal orthosis of claim 1, wherein the first front closure defines first and second clamping sections arranged to removably secure to opposed sides of the foldable portion of the first belt member.

4. The spinal orthosis of claim 1, wherein the rear panel includes a closure system having at least one tensioning element with a handle, the at least one tensioning element extending from the closure system and the handle is removably securable to a first surface of the first front closure.

5. The spinal orthosis of claim 1, further comprising a rigid plate having a connector removably securing to an inner side of the rear panel.

6. The spinal orthosis of claim 1, wherein the rear panel includes a closure system and a stretchable cover extending from the first and second sides, the cover stretching or retracting over a variable distance according to adjustment of the closure system.

7. The spinal orthosis of claim 1, wherein the rear panel includes a cover stretchable over a variable distance defined between the first and second sides thereof, the first and second belt members formed from a substantially non-stretchable material such that pulling the second ends of the first and second belt members causes the variable distance to increase, and releasing the second ends causes the cover to retract to a predetermined distance.

8. The spinal orthosis of claim 1, wherein the rear panel includes a closure system and a first end of an elongate tensioning element engages the closure system and a handle secures to a second end of the tensioning element, the first belt member forming a channel including a first opening proximate the closure system and a second opening, the channel being formed between first and second surfaces of the first belt member such that the tensioning element enters the channel at the first opening and exits by the second opening such that the second end of the tensioning element extends beyond the second opening.

9. The spinal orthosis of claim 1, wherein the second ends of the first and second belt members each include fasteners extending from an outer side of the spinal orthosis for securing to a surface of the first and second belt members on the outer side of the spinal orthosis.

10. The spinal orthosis of claim 1, wherein the first and second belt members have a thickness in the range of 1.5 to 2.5 mm.

11. A method for resizing a spinal orthosis including a rear panel having first and second sides, a first belt member having a first end secured to the first side of the rear panel and a resizable second end, and a second belt member having a first end secured to the second side of the rear panel and a resizable second end, the method comprising the steps of:
using a sizing device having first and second positioning elements for establishing a predetermined distance between the second ends of the first and second belt members.

12. The method of claim 11, further comprising:
extending a portion of the second end of the first belt member over the first positioning element to determine a resized length of the first belt member between the rear panel and the first positioning element.

13. The method of claim 12, further comprising:
securing the second end of the first belt member over a peripheral surface of the first belt member to retain the resized length of the first belt member and form a foldable portion of the first belt member;
removing the sizing device from the first belt member after the resized length is established.

14. The method of claim 13, further comprising:
securing a first front closure to the foldable portion of the first belt member.

15. The method of claim 12, further comprising:
extending a portion of the second end of the second belt member over the second positioning element to determine a resized length of the second belt member between the rear panel and the second positioning element;
tensioning both the first and second belt members by pulling the second ends away from the first and second positioning elements and toward the rear panel.

16. A kit for sizing a spinal orthosis including a rear panel having first and second sides, a first belt member having a first end secured to the first side of the rear panel and a resizable second end, and a second belt member having a first end secured to the second side of the rear panel and a resizable second end, the kit comprising:
a sizing device having first and second positioning elements for establishing a clearance defined by a predetermined distance between the second ends of the first and second belt members.

17. The kit of claim 16, wherein the first and second positioning elements are first and second rods spaced apart by a cord having a length extending the predetermined distance between the first and second rods.

18. The kit of claim 16, wherein the sizing device is a board having a main portion and the first and second positioning elements extend from the main portion, the first and second positioning elements are spaced apart by a center section with a width forming the predetermined distance, first and second grooves are formed by the board and separate the first and second positioning elements, respectively, from the center section.

19. The kit of claim 16, further comprising first and second belt expanders arranged for securing to the second end of the first and second belt members, the first and second belt expanders having first and second ends each bearing fasteners for securing to the first and second belt members.

* * * * *